(12) United States Patent
Simon

(10) Patent No.: US 6,592,590 B2
(45) Date of Patent: Jul. 15, 2003

(54) DEVICE FOR INSERTING AND REMOVING A BONE NAIL

(75) Inventor: Bernd Simon, Kiel (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 09/910,327

(22) Filed: Jul. 20, 2001

(65) Prior Publication Data
US 2002/0026196 A1 Feb. 28, 2002

(30) Foreign Application Priority Data

Jul. 22, 2000 (DE) .......................... 200 12 735

(51) Int. Cl.⁷ .............................................. A61B 17/56
(52) U.S. Cl. ................................ 606/99; 173/90; 81/20; 81/23
(58) Field of Search ....................... 606/86, 99, 100, 606/104, 53; 173/90; 81/20, 23, 27

(56) References Cited

U.S. PATENT DOCUMENTS 3,818,514 A * 6/1974 Clark .......................... 206/438
3,857,389 A * 12/1974 Amstutz ....................... 269/90
4,222,382 A * 9/1980 Antonsson et al. ......... 606/100
5,156,606 A * 10/1992 Chin ........................... 606/100
5,584,837 A * 12/1996 Petersen ....................... 606/86
5,690,636 A * 11/1997 Wildgoose et al. ......... 606/100
5,906,210 A * 5/1999 Herbert ....................... 128/898
5,913,860 A * 6/1999 Scholl ......................... 606/100

FOREIGN PATENT DOCUMENTS

| DE | GM 1 863 282 | 12/1962 |
|---|---|---|
| DE | 197 04 836 A1 | 9/1998 |
| EP | 0 528 128 | 11/1996 |

* cited by examiner

Primary Examiner—Eduardo C. Robert
(74) Attorney, Agent, or Firm—Lerner, David, Littenberg, Krumholz & Mentlik, LLP

(57) ABSTRACT

An instrument for inserting and removing a bone nail connected to a rod is provided. The instrument includes a head element that has a guide surface for guiding the head element along the guide rod. The head element is cylindrical or barrel-shaped, and the guide surface is formed by an axial channel in the head element, and has a lateral access which is formed in the head element. The access is used to introduce the guide rod into the axial channel, in such a way that the head element is secured to prevent it from being removed from the guide rod in the lateral direction.

19 Claims, 2 Drawing Sheets

DEVICE FOR INSERTING AND REMOVING A BONE NAIL

BACKGROUND OF THE INVENTION

The invention relates to a device for inserting and removing a bone nail, along a guide rod that is connected with the bone nail or with an instrument that is connected with the bone nail.

The use of bone nails to aid in the healing of fractures is known. European patent EP 0 528 128 B1 shows a locking nail to correct femur fractures in the middle and trochanter region. In order to drive the nail in or remove it, the locking nail is screwed into an aiming or setting device at its end. For orientation for the operator, the aiming device has a guide rod that points in the longitudinal direction of the nail to be set in.

SUMMARY OF THE INVENTION

During the setting process of the locking nail, a medium pressure is exerted on the setting device, driving the nail into the bone. Small rotational movements of the locking nail facilitate its replacement. As a rule, driving the nail in with a hammer should be avoided, since the risk of damaging the bone to be treated is too great. Sometimes, however, it is necessary to drive the nail in with light taps. For this, it is known to use a slit or slotted hammer. The hammer, which is guided along the guide rod with the slit, ensures that the force applied with the hammer taps runs in the longitudinal direction of the nail. When the locking nail is supposed to be removed from the bone, for example, the guide rod is provided with a stop at the end pointing away from the bone. The slit hammer is arranged on the guide rod and the locking nail is removed by tapping the hammer against the end of the guide rod.

The invention is based on the task of making available a device for driving in and removing a bone nail along a guide rod, which device has a structure such that guidance of the tool is made reliably possible, while providing ease of handling.

The device according to the invention, for driving in and removing a bone nail of the type indicated above, is secured to prevent lateral removal from the guide rod. Lateral access to an axial channel makes it possible to set the head element against the guide rod, and to secure it there to prevent it from accidentally slipping off, or to prevent missing the bone nail with the hammer. Such a secured guide is particularly advantageous when removing the nail. The cylindrical or barrel-shaped structure of the head element gives the operator a clear view of the locking nail, i.e. its aiming device, when using the device according to the invention. It is preferred that the cylindrical head element is provided with tapping surfaces at its faces.

In the preferred embodiment of the invention, the lateral access possesses three segments connected with it, where a central segment stands perpendicular to the channel and two end segments that each follow the central segment run in an axial direction along the channel, in each instance, where the end segments are aligned in such a way that the head element set onto the guide rod with the central segment is put into a secured, locked position by means of a rotation during which the end segments take up the guide rod. Preferably, the central segment is at 90° perpendicular to the guide direction, so that a 90° rotation of the head element is necessary in order to achieve the locked position. The head element can be provided with a handle element that preferably points in the radial direction of the head element.

BRIEF DESCRIPTION OF THE DRAWINGS

A preferred embodiment of the device according to the invention is explained in greater detail on the basis of the following figures. These show.

DETAILED DESCRIPTION

Figure 1:
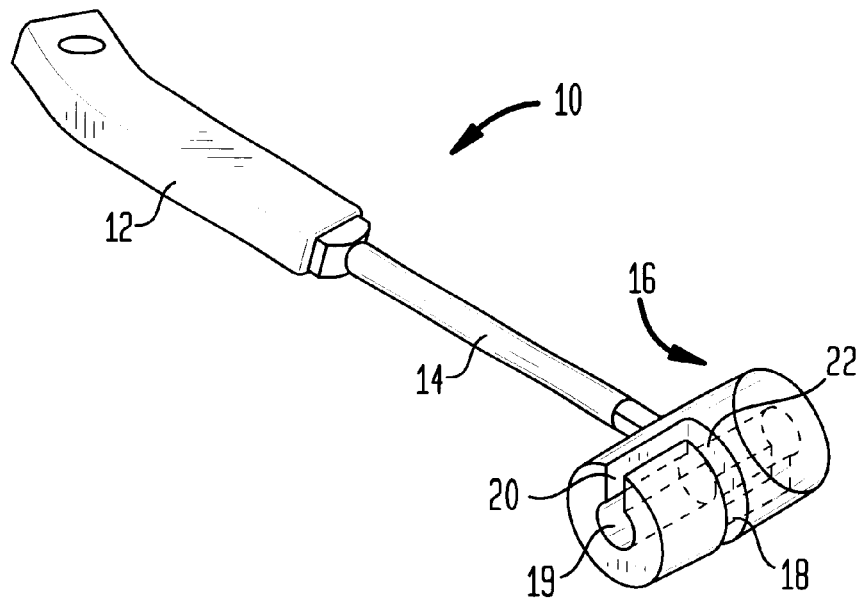
FIG. 1 is a hammer according to the invention in a perspective view.

FIG. 1 shows a hammer 10 according to the invention with a handle element that is composed of a hand piece 12 and a shaft 14 that projects from it. The hand piece 12 possesses a rectangular cross-section and is slightly angled at its free end. In the preferred embodiment, the shaft 14 that projects from the hand piece 12 is thinner and possesses an essentially round cross-section. The shaft 14 ends at the head 16, which has an essentially cylindrical shape in the preferred embodiment shown. If the head element 16 is not provided with a handle element, the head element can be held along its circumference wall.

The head 16 is provided with an access opening 18, which possesses end segments 20 and 24 as well as a central segment 22. In the view shown, the second end segment 24 is covered. The access 18 has a width that is greater than the diameter of the guide rod. The central segment 22 of the access 18 is perpendicular to the longitudinal direction of the head element 16, and extends from the surface to beyond the center longitudinal axis of the cylinder. The access 18 leads to the axial channel 19, which runs through the head element in an axial direction.

Figure 2:
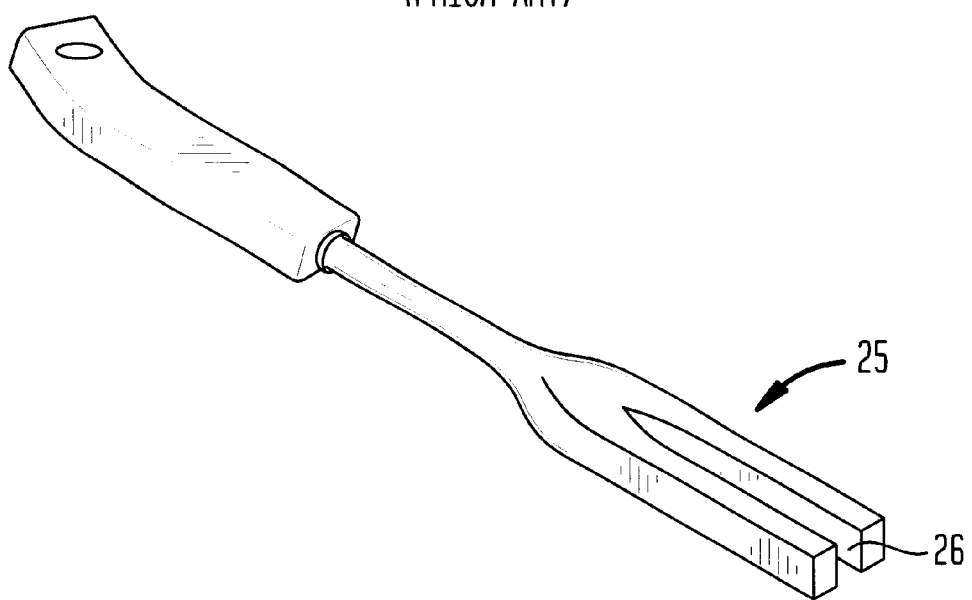
FIG. 2 is a slit hammer from the known state of the art.

FIG. 2 shows a slit hammer from the state of the art. The head element 25 is shaped essentially in cube form. The slit 26 is sized to hold the guide rod 28 which extends along the longitudinal direction of the head.

Figure 3:
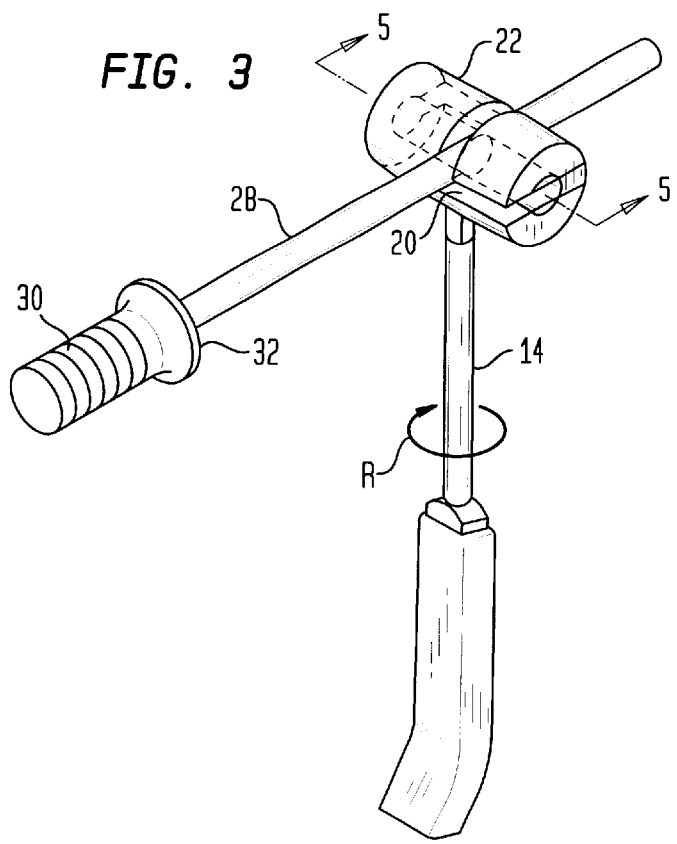
FIG. 3 is a hammer according to the invention, set onto the guide rod.
Figure 4:
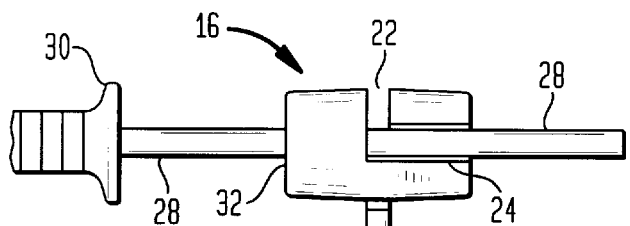
FIG. 4 is a hammer according to the invention, in its position secured on the guide rod.
Figure 5:
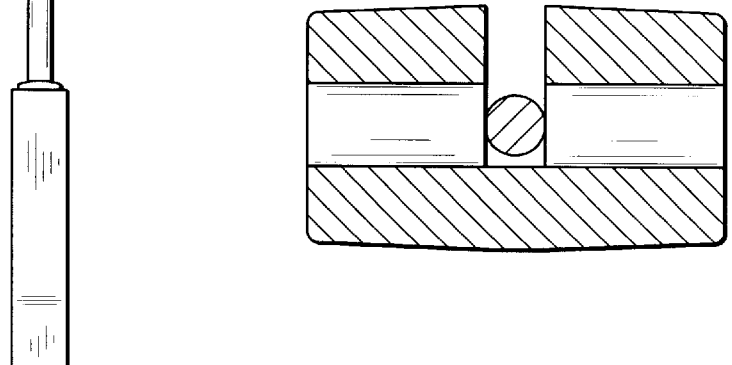
FIG. 5 is a cross-sectional view of the hammer shown in FIG. 3 along lines 5—5.

FIGS. 3 and 4 explain how the hammer according to the invention is attached to the guide rod 28. In this connection, parts that are the same as in FIG. 1 are indicated with the same reference symbol. The guide rod 32 has a tapping element 30 on one side, against which the hammer is tapped to remove the bone nail. The guide rod 28 is connected with one end of the bone nail at its end (not shown). To drive the bone nail in, an additional tapping element (not shown) can be arranged between the bone nail end and the head 16.

The central segment slot or slit 22 of access 18 intersects the continuous longitudinal bore for receiving rod 28 formed by oppositely extending channel or bore portions 20, 24 which portions extend on opposite sides of the barrel or cylinder 16 from opposite ends thereof to the central segment 22. Each end portion 20, 24 is partially open in the lateral direction to opposite sides of the head 16. Thus, rod 28 can be placed in slot 22 across head 16 and rotated 90° (into alignment with the longitudinal axis of rod 28) to lock the hammer 16 on the rod 28.

To drive the nail in, the hammer is set onto the guide rod 28 with its central segment. By means of a rotational movement around the longitudinal axis of the shaft 14, in a direction of the arrow A, the slits or end segments 20, 24 capture the guide rod 28. The secured position is shown in FIG. 4. The hammer can be guided along the guide rod into the nail end with the head element 16, thereby preventing the hammer from being accidentally removed from the guide rod 28. The face 32 serves as a tapping surface in this position, interacting with the tapping element 30, to remove the bone nail. Removal of the hammer according to the invention from the guide rod takes place by means of a rotational and pulling movement.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A hammer for driving in and removing a bone nail connected to a guide rod, the hammer comprising a head element that has a guide surface for guiding the head element along the guide rod, the head element is generally cylindrical or barrel-shaped, and the guide surface is formed by an axial channel in the head element, the head element includes an access channel formed in the head element via which the guide rod is introduced into the axial channel, the access channel extends in a direction transverse to said axial channel and intersects therewith.

2. The hammer according to claim 1, wherein the axial channel has three segments of which a central segment is formed by the transverse access channel and first and second end segments, each end segment being axially aligned and extending in an opposite direction from the central segment each segment being open in opposite transverse directions, the first and second segments have guide rod contacting surfaces facing in opposite transverse directions.

3. The hammer according to claim 2, wherein the access channel essentially forms a right angle with the end segments of the axial channel.

4. The hammer according to claim 3, wherein the access channel is centered on the head element in the axial direction.

5. The hammer according to claim 2, wherein the access channel is centered on the head element in the axial direction.

6. The hammer according to claim 1, wherein a handle element is provided on the head element.

7. The hammer according to claim 6, wherein the head element is connected with the handle element in the transverse direction.

8. The hammer according to claim 7, wherein the head element has end tapping surfaces.

9. The hammer according to claim 6, wherein the head element has end tapping surfaces.

10. An instrument for inserting and removing a bone nail from a bone, comprising:
a guide rod having a first end for coupling to an end of the nail;
a hammer element with contact faces removably coupled to said guide rod for sliding engagement therewith in a longitudinal direction, the hammer element having channels partially open in opposite directions transverse to said longitudinal direction and aligned along an axis of said hammer element extending in said longitudinal direction and an access channel extending in a direction transverse to said longitudinal direction intersecting said partially open channels.

11. The instrument as set forth in claim 10 wherein an end of said rod opposite said first end includes a handle.

12. The instrument as set forth in claim 10 wherein the access channel extends perpendicularly to said longitudinal direction.

13. The instrument as set forth in claim 10 wherein the hammer element has end tapping surfaces.

14. The instrument according to claim 10, wherein the axial channel has three segments of which a central segment is formed by the access channel and first and second end segments, each end segment being axially aligned and extending in an opposite direction from the central segment in an axial direction, the first and second segments intersect with the central segment and have guide rod contacting surfaces facing in opposite transverse directions with respect to said longitudinal direction.

15. The instrument according to claim 14, wherein the access channel essentially forms a right angle with the end segments of the axial channel.

16. The instrument according to claim 15, wherein the access channel is centered on the head element in the axial direction.

17. A method for inserting or removing a bone nail from a bone, comprising:
coupling a rod to a first end of the bone nail;
attaching a removable hammer element to said rod for sliding engagement therewith in a longitudinal direction, said hammer element having partially open channels aligned along an axis of said hammer element extending in said longitudinal direction and an access channel extending in a direction laterally of said longitudinal direction intersecting said partially open channels;
inserting said rod in said access channel in a direction laterally to said longitudinal direction and rotating said hammer element so that said partially open channels are in alignment with said rod;
sliding said hammer along said rod along said partially open channels; and
contacting a surface connected to said nail with said hammer element to either remove or insert the nail.

18. An instrument for inserting and removing a bone nail from a bone, comprising:
a guide rod having a first end for coupling to an end of the nail;
a hammer element with contact faces, said hammer element having laterally open channel having guide rod contacting surfaces extending along an axis and a guide rod access channel extending transverse to the axis and intersecting with said laterally open channel, said open channel having three segments in which a central segment is formed by the transverse access channel and first and second end segments, each end segment extending in an opposite direction from the central segment, said first and second segments have said laterally open guide rod contacting surfaces facing in opposite transverse directions with respect to said axis of said rod contacting channel.

19. The instrument as set forth in claim 18, wherein the access channel extends perpendicularly to said longitudinal direction.

* * * * *